United States Patent [19]

Zembrodt

[11] Patent Number: 4,948,047
[45] Date of Patent: Aug. 14, 1990

[54] AIR FRESHENER WITH MICROPOROUS MEMBRANE

[75] Inventor: Anthony R. Zembrodt, Covington, Ky.

[73] Assignee: Drackett Company, Cincinnati, Ohio

[21] Appl. No.: 231,759

[22] Filed: Aug. 12, 1988

[51] Int. Cl.⁵ ............................................. A61L 9/12
[52] U.S. Cl. .................................................... 239/34
[58] Field of Search ...................... 239/34, 37, 43, 44, 239/57, 145

[56] References Cited

U.S. PATENT DOCUMENTS

| | | | |
|---|---|---|---|
| 2,766,066 | 10/1956 | Hopson et al. | 239/44 |
| 3,169,705 | 2/1965 | Geiger | 239/43 |
| 3,254,841 | 6/1966 | De Loncker, Sr. | 239/44 |
| 4,173,604 | 11/1979 | Dimacopoulos | 239/45 |
| 4,356,969 | 11/1982 | Obermayer et al. | 239/56 |
| 4,727,840 | 4/1988 | Nigro | 239/43 |
| 4,809,912 | 3/1989 | Santini | 239/60 |

Primary Examiner—Andres Kashnikow
Assistant Examiner—Karen B. Merritt
Attorney, Agent, or Firm—G. Warzecha; S. Nolan

[57] ABSTRACT

A passive dispenser of volatile liquid fragrance composition from a container thereof. The container has an orifice at its bottommost point and an isotatic hydrophobic polypropylene membrane covering the orifice. The membrane permits passage of the liquid fragrance composition therethrough in the liquid phase in order to enable the composition of the liquid transmitted through the membrane to be substantially the same as that of the liquid within the container.

5 Claims, 1 Drawing Sheet

AIR FRESHENER WITH MICROPOROUS MEMBRANE

BACKGROUND OF THE INVENTION

1. Field of the Invention

The invention generally relates to controlled rate release devices for volatile materials. More particularly, the invention relates to air fresheners which operate upon the principle of liquid phase transfer of a liquid fragrance composition through a microporous membrane.

2. Description of the Prior Art

Air fresheners are well known for the purpose of dispensing odorizing or deodorizing active ingredients into a particular area such as a room in a house, office, etc. Both passive and active air fresheners are available; the latter actively emitting a perfumed or deodorizing ingredient at certain intervals and the former relying on evaporation of similar, volatile ingredients. Residential air fresheners are generally passive and available in a variety of perfume-based forms and fragrances to mask unpleasant household odors and/or to provide pleasant odors. Passive air fresheners generally are produced with their active ingredients in a gel or liquid form and operate on the principle of evaporation of a perfume-based volatile liquid from a gelled mass or from a container via a wick and/or an emanator pad exposed to ambient air.

In order to be effective, passive air fresheners should ideally deliver the desired fragrance at a uniform rate over an extended period of time—i.e., a zero-order rate of release. A zero-order release rate is an essentially constant rate of release of active ingredient that is independent of either the amount of the active ingredient or its vapor pressure. However, many prior art air fresheners initially deliver a large amount of fragrance and subsequently deliver progressively less fragrance. The initial large dose is often objectionable and more than is necessary, while the later small dose is often undetectable and inadequate. To the extent all of the active ingredient is not dispensed at a constant rate, the non zero-order rate devices are costly and wasteful.

U.S. Pat. No. 4,445,641 (Baker et al.) discloses a controlled release dispenser supposedly capable of delivering essentially all of an active ingredient at a selected zero-order rate of release over a broad range of release rates. Patent '641 describes a dispenser having a microporous liquid retaining reservoir portion encased within a release rate-controlling polymeric membrane. The microporous reservoir retains liquid by capillary action. Polypropylene and other materials are suggested as suitable for the polymeric membrane and the patent also suggests the controlled release of perfumes, deodorizers and a variety of other active ingredients through such polymeric membranes.

While the Baker et al. patent does suggest utilizing polypropylene membranes with perfumes, the membranes disclosed must first be impregnated with a liquid active ingredient and the membranes disclosed are only suitable for dispensing active ingredient at a rate on the order of micrograms per day. To be effective as an air freshener the rate should be on the order of 1-20 milligrams per hour to fragrance a room of 1000 ft.$^3$ Additionally, impregnation of the membranes is an extra manufacturing step that has been found unnecessary with the present invention.

In addition to the desirability of a zero-order rate of release, it is also desirable that the fragrance released by air fresheners be uniform and undistorted over the life of the dispenser.

It is well known that the fragrant materials of air fresheners include a significant amount of volatile perfume ingredients in various proportions. Typically, the perfumes incorporated in the compositions used in air fresheners are mixtures of organic compounds admixed so that the combined odors of the individual components produce a pleasant or desired fragrance. While perfumes are generally mixtures of various materials, individual compounds may also be used as the perfume ingredient. Typical compounds for use in mixtures or individually, include methyl salicylate, d-limonene and the like.

The perfume compositions generally contain several "notes", each having different volatility rates and therefore being subject to the process of chromatography which may result in a differential distribution of the notes at various times. The various notes include a main note or the "bouquet" of the perfume composition, modifiers which round off and accompany the main note, fixatives including odorous substances that lend a particular note to the perfume throughout each of the stages of evaporation, substances which retard evaporation, and top notes which are usually low-boiling, fresh-smelling materials.

Perfumery raw materials may be divided into three main groups: (1) the essential oils and products isolated from these oils; (2) products of animal origin; and (3) synthetic chemicals. Many of these materials include such substituent groups as the carbonyl group in aldehydes and ketones; the hydroxyl groups in alcohols; the acyl group in esters; the C=O groups in lactones; nitrile groups, and the oxy moiety in ethers.

The essential oils consist of complex mixtures of volatile liquid and solid chemicals found in various parts of plants. Mention may be made of oils found in flowers, e.g., jasmine, rose, mimosa, and orange blossom; flowers and leaves, e.g., lavender and rosemary; leaves and stems, e.g., geranium, patchouli, and petitgrain; barks, e.g., cinnamon; woods, e.g., sandalwood and rosewood; roots, e.g., angelica; rhizomes, e.g., ginger; fruits, e.g., orange, lemon, and bergamot; seeds, e.g., aniseed and nutmeg; and resinous exudations, e.g., myrrh. These essential oils consist of a complex mixture of chemicals, the major portion thereof being terpenes, including hydrocarbons of the formula $(C_5H_8)_n$ and their oxygenated derivatives. Hydrocarbons such as these give rise to a large number of oxygenated derivatives, e.g., alcohols and their esters, aldehydes and ketones. Some of the more important of these are geraniol, citronellol and terpineol, citral and citronellal, and camphor. Other constituents include aliphatic aldehydes and also aromatic compounds including phenols such as eugenol. In some instances, specific compounds may be isolated from the essential oils, usually by distillation in a commercially pure state, for example, geraniol and citronellal from citronella oil; citral from lemon-grass oil; eugenol from clove oil; linalool from rosewood oil; and safrole from sassafras oil. The natural isolates may also be chemically modified as in the case of citronellal to hydroxy citronellal, citral to ionone, eugenol to vanillin, linalool to linalyl acetate, and safrol to heliotropin.

Animal products used in perfumes include musk, ambergris, civet and castoreum, and are generally provided as alcoholic tinctures.

The synthetic chemicals include not only the synthetically made, and naturally occurring isolates mentioned above, but also include their derivatives and compounds unknown in nature, e.g., isoamylsalicylate, amylcinnamic aldehyde, cyclamen aldehyde, heliotropin, ionone, phenylethyl alcohol, terpineol, undecalactone, and gamma nonyl lactone.

Perfume compositions as received from the perfumery house may be provided as an aqueous or organically solvated composition, and may include as a hydrotrope or emulsifier a surface active agent, typically an anionic or nonionic surfactant, in minor amount. The perfume compositions are quite usually proprietary blends of many different fragrance compounds to achieve a particular odoriferous effect.

Typically, perfume compositions contain an effective fragrancing amount of 0 to 100% by weight of the fragrance ingredient. Generally, perfume ingredient(s) are used at concentrations of about 0.1 to about 75 wt.%, based on total composition weight. The balance of the composition being one or more diluent(s), surfactant(s) and the like.

In order to produce an air freshener capable of delivering a uniform odor over an extended period of time, it is necessary to try to avoid the process of chromatography by providing a means by which all the various notes of the perfume may remain in the same proportions over time. It has been found that transmission of a perfume based composition in the liquid phase through a microporous membrane having particular characteristics produces a liquid film of the composition on one side of the membrane and the various notes of the perfume are in substantially the same proportions in the film as in the composition on the other side of the membrane. It should be noted that, as used herein, the term "liquid phase transmission" does not include capillary action like that shown in the aforementioned Baker et al. patent. Chromatography occurs in such capillary action systems.

It has been noted that when liquid phase diffusion or transmission takes place (i.e., liquid passing through the membrane or film) the character of the fragrance does not vary with time. That is, the composition of the first liquid portions passing through is substantially the same as the later portions.

Membranes have long been used in delivery systems for volatile materials. One example of this is the aforementioned Baker et al. patent. Other examples are U.S. Pat. Nos. 3,951,622 (Wilk), 4,248,380 (Lee et al.), 4,614,299 (Van Lovern et al.). All of the dispensers shown in these patents utilize the principle of vapor phase migration of liquid active ingredients through a permeable membrane. However, U.S. Pat. No. 4,158,440 (Sullivan et al.) does show a dispenser utilizing the liquid phase transfer of liquid active ingredients through a specific type of permeable membrane --cellulose triacetate. Sullivan et al. did disclose that a particular microporous polypropylene film known as CELGARD$^R$, produced by the Celanese Corporation, was also suitable in place of cellulose triacetate. However, Sullivan et al. indicates that CELGARD$^R$ acts as a liquid barrier and is permeable only to vapor which volatilizes from the liquid substance within the dispenser. This is a feature of CELGARD$^R$ that is also identified by the manufacturer. As will be understood below, the invention operates in spite of this contrary teaching.

U.S. Pat. No. 3,785,556 (Watkins) also shows a package employing liquid phase transfer through a polyethylene or polypropylene envelope via the mechanism of permeation—i.e., "diffusion by absorption not to be confused with porosity or capillarity" (1:64-67). However, it is known that membranes of conventional polypropylene (either cast or oriented) change the character and intensity of fragrances for both liquid and vapor phase transport mechanisms.

In spite of the teaching to the contrary in Sullivan et al., above, it has now been found that the invention which is the subject hereof operates with CELGARD$^R$ to produce a dispenser of volatile fragrant liquid ingredients which migrate through the CELGARD$^R$ membrane in liquid phase rather than vapor phase.

This particular membrane has a thickness of 0.5 to 5 mil with no fillers, plasticizers or extenders and has the following properties: 14000 to 20000 psi MD tensile strength, 1400 to 2000 psi TD tensile strength, 100,000 cycle folding endurance, 1 lb MD tear strength, a density of 0.28 to 0.32 oz/cubic inch, an area of 50000 to 60000 square inches per pound with 70% opacity, a moisture transmission rate of 4000 to 6000 g/square meter/day (BW method, inverted cup water method), a pore density of $10 \times 10^9$ pores/square centimeter to $7 \times 10^9$ pores/square centimeter and a resistance to air of 9 to 35 Gurley seconds. While the CELGARD$^R$ membrane is preferred, other membranes having these or similar properties can also be employed.

It has been found that a vent hole allowing pressure equalization inside the container is advantageous. The perfume composition used in the preferred embodiment is, for example, a neat oil or a blended perfume which will be transported across the surface of the membrane at a rate of 1 to 20 mg per hour, preferably 3-10 mg per hour, and more preferably 4-7 mg per hour, sufficient to give the desired concentration of fragrance.

The aforementioned Wilk patent discloses a permeable membrane through which a fragrance (including an essential oil and an alcohol having a molecular weight below 100, e.g. ethanol) passes substantially unchanged. However, the transmission through the membrane is only vapor phase transmission and the device is, apparently for this reason, limited to use with fragrance compositions including an essential oil and an alcohol having a molecular weight below 100. While one embodiment of Wilk appears to show a liquid fragrance within a pouch made entirely of the permeable membrane, there is no elaboration on the method of operation of this embodiment. It is assumed this embodiment also employs vapor phase transmission.

It is an object of this invention to provide a passive dispenser of volatile liquid ingredients which enables substantially all of the liquid ingredients to be dispensed over a period of time.

It is a further object of this invention to provide a passive dispenser of volatile liquid ingredients capable of dispensing same at a substantially uniform rate over the life of the dispenser.

It is another object of this invention to provide a passive dispenser capable of transmitting a composition of volatile fragrant liquid ingredients in liquid phase through a membrane in order to overcome the tendency of the various constituents of the liquid to volatilize at different rates before being exposed to the ambient environment. It is also an object of this invention to enable such liquid phase transmission while using, as the fragrance composition, a perfume having no essential oils one having, a trace amount of essential oils, or an essential oil itself.

It is another object of this invention to provide a passive dispenser capable of transmitting a volatile fragrant liquid ingredient in its liquid phase through a membrane in order to maintain the character and intensity of the fragrance before and after the transmission through the membrane.

SUMMARY OF THE INVENTION

These and other objects of this invention are achieved by the preferred embodiment thereof which is a dispenser for dispensing a liquid fragrance composition at a substantially constant rate comprising: a container for containing said liquid fragrance composition, said container having an orifice through which said composition may flow; means for supporting said container in a position such that said orifice is beneath said liquid fragrance composition; and a liquid permeable, microporous membrane secured within said orifice, said microporous membrane enabling said liquid fragrance composition to flow therethrough at a predetermined rate, said microporous membrane being continually in contact with said liquid fragrance composition during the useful life of said dispenser, said liquid fragrance composition appearing, upon attainment of steady state equilibrium conditions, in liquid form on the exterior surface of said membrane and evaporating therefrom, the composition of said liquid form being, at a given point in time, substantially the same as that of the liquid fragrance composition remaining within the container.

DESCRIPTION OF THE PREFERRED EMBODIMENT

Figure 1:
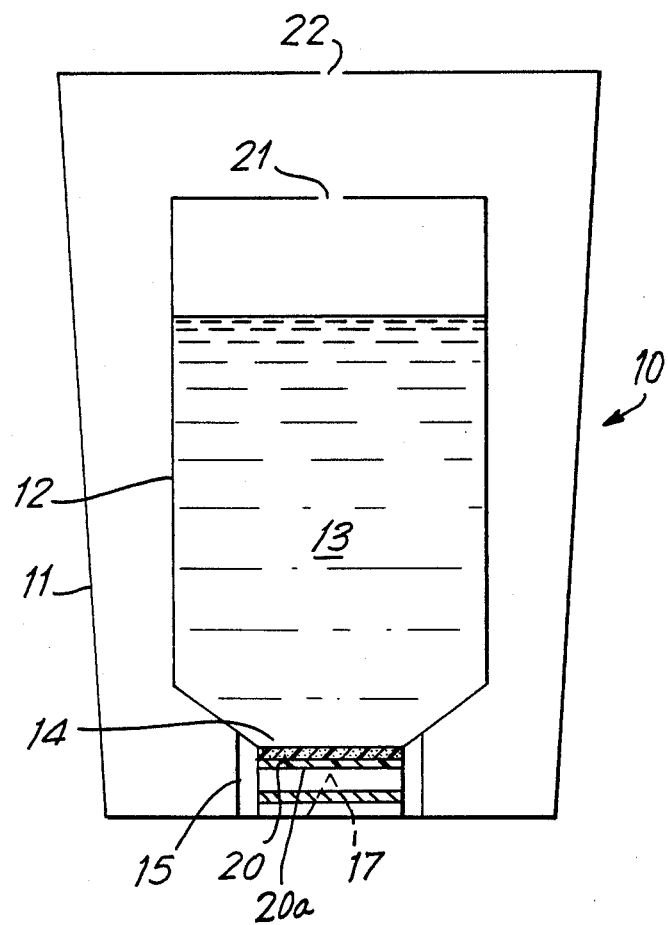
FIG. 1 is a schematic side elevational cross-sectional view of a dispenser constructed in accordance with the principles of this invention.

As shown in FIG. 1, a dispenser 10 constructed in accordance with the principles of this invention comprises a shell 11 and a container 12 having an active ingredient 13 and opening 14 over which is secured a particular polypropylene film or membrane 20. Container 12 may be a conventional container having a threaded neck sealed with a cap (not shown). This type of structure would permit refills to be provided separately from the dispenser shell. Because of the liquid phase transmission of the active ingredient, container 12 is inverted within the dispenser and supported by support member 15. A foil seal 16 may seal container 12 prior to use and a spike 17 or similar means may be provided to penetrate the foil.

The membrane of the preferred embodiment is CELGARD$^R$, manufactured by the Celanese Corporation. CELGARD$^R$ is an isotatic hydrophobic polypropylene having submicron pores. The pores are described by the manufacturer as being slit-like and can be thought of as providing a tortuous channel leading from the inner surface of the membrane facing the interior of container 12 to the outer surface. These pores combine with the inherent hydrophobic characteristics of polypropylene to prevent high-surface tension liquids such as liquid water from passing therethrough. The hydrophobic films generally permit low surface-tension liquids to flow therethrough provided the surface tension of the liquid is generally less than 35 dyne/cm.

The liquid fragrance compositions suitable for use in dispenser 10 may be any one of a variety of low surface-tension liquids containing one or more conventional perfume ingredient(s).

The surface area of the outer surface of membrane 20 provides the control over the amount of liquid which is transmitted from the container in a given unit of time. It is generally desired to release 3-8 mg of perfume per hour in a 1000 cubic foot room in order to give rise to the appropriate fragrance character and intensity. The necessary surface area of the membrane is a function of the volatility of the perfume and the size of the space to be fragranced. For relatively non-volatile perfumes, an additional emanator pad 20a may be used in conjunction with the membrane to increase the evaporative surface area to release the required amount of perfume. The emanator pad may be placed in contiguous contact with the membrane to absorb, by capillary action, liquid which has passed through the membrane.

It has been found advantageous to provide container 12 with a vent hole 21 so the vacuum produced by the continually decreasing volume within the container will not retard the flow through the membrane. If a shell 11 is used, there should also be a vent 22 in the shell.

CELGARD$^R$ is produced in various forms and sizes and, while all are suitable for use in the invention depending upon the choice of liquid fragrance composition, the preferred embodiment incorporates CELGARD$^R$ 2500 which is hydrophobic and has 0.04 $\mu$ pores.

The performance of the device of the invention was quantitatively compared to the membrane transmission device in the aforementioned Wilk patent. The character and intensity of the test perfume transmitted were measured using "Magnitude Estimation". This technique is described in H.R. Moskowitz, *Journal of Food Quality*, 3 (1977) pp. 195-227 and J.H. Pearce, et al., "Evaluation of Three Scales of Methods for Hedonics", *Journal of Sensory Studies*, 1 (1986) pp. 27-46.

The procedure requires several panelists to rate the perfume's intensity and character (what it smells like) and, at the same time, to rate a control. Magnitude Estimation is an industry accepted ratio scaling technique which allows each of the panelists to determine his or her own scale. Since what is being measured is a subjective characteristic, many panelists are required to rate the sample and statistical methods are used to determine if a statistically significant difference exists between the sample and the control.

An experiment was conducted to compare the character of the fragrance transmitted in liquid phase through CELGARD$^R$ and that transmitted in vapor phase through a conventional 1.25 mil polypropylene film (as shown in Wilk patent). The results are tabulated in Table I. The character was determined after 8 days and after 34 days with varying samples as noted below. A rating of 40 is required to indicate a slight difference in character by Magnitude Estimation.

TABLE I

| Sample | Day | Character Difference* |
| --- | --- | --- |
| CELGARD ® 2500 (.04μ) | 8 | 7 |
| CELGARD ® 2500 (.04μ) | 34 | 14 |
| CELGARD ® 2400 (.02μ) | 8 | 0.5 |
| CELGARD ® 2400 (.02μ) | 34 | 15 |
| PP** Film sample #1 | 8 | 44 |
| PP Film sample #1 | 34 | 22 |
| PP Film sample #2 | 8 | 28 |

TABLE I-continued

| Sample | Day | Character Difference* |
|---|---|---|
| PP Film sample #2 | 34 | 48 |

*Compared to control
**Polypropylene

It should be noted that the character of the fragrance transmitted through CELGARD$^R$ in accordance with the terms of this invention was much less affected by the transmission than the fragrance transmitted through conventional polypropylene.

Intensity was tested separately and it was found that the invention improves this parameter as well. The experiment for intensity sampled the air in a box ($3' \times 3' \times 3'$) using head space technology and the results are tabulated in Table II. The collected sample was injected into a G.C.; thus, the larger the number obtained the more intense the perfume.

TABLE II

| Day | CELGARD ® (0.040μ pores) | Wilk Device (1.25 mil) |
|---|---|---|
| 8 | 49000 | 14000 |
| 36 | 76000 | 3000 |

Examples of liquid flow rates through various samples of CELGARD$^R$ 2400 membrane are listed below in Table III.

TABLE III

| Experiment | Diameter of membrane (inches) | Diffusion Rate (mg/hr) | Liquid |
|---|---|---|---|
| 1 | ⅜ | 6 | Proprietary neat oil; H&R (Haarman and Reimer) A-60061A |
| 2 | ⅜ | 10 | Methyl salicylate |
| 3 | ¾ | 120 | d-limonene |
| 4 | ½ | 140 | Proprietary neat oil (from Florasynth) |
| 5 | ¼ | 2 | Proprietary neat oil (from Florasynth) |
| 6 | ¼ | 6 | Proprietary neat oil C (from Florasynth) |
| 7 | ¼ | 3 | Proprietary neat oil (from Florasynth) |
| 8 | ¼ | 1 | Perfume (H&R A60061A thickened with Monafax 785 (1:1) |
| 9 | ⅜ | 6 | Neodol 1 (ethoxylated) alcohol) |
| 10 | ¾ | 150 | OMS*/H&R A60061A (1:1) |
| 11 | ⅜ | 3 | Perfume (H&R A60061A) w/blotter |
| 12 | ⅜ | 2 | Perfume (H&R A60061A) w/wing emanator |

*Odorless Mineral Spirits

As can be seen variable flow and evaporation rates are possible with differing surface areas and differing pore sizes. Thus, essentially any desired delivery rate of liquid fragrance composition may be obtained depending upon the size of the space to be treated as well as other variables.

In order to increase evaporation rates from less volatile perfumes one can use emanator pads made of cellulose or other material to increase the surface area from which evaporation can occur. While the use of emanator pads is known, the use of CELGARD$^R$ produces a unique feature since it acts as a metering device or valve that controls the amount of perfume that can come in contact with the emanator pad.

It has been found that a vent hole should be used to allow atmospheric pressure to be equalized on both sides of the membrane. If a partial vacuum exists then the flow rate will be effected.

It will be understood by those skilled in the art that numerous modifications and improvements may be made to the preferred embodiment of the invention disclosed herein without departing from the spirit and scope thereof.

I claim:

1. A dispenser for dispensing a liquid fragrance composition at a substantially constant rate comprising:
   (a) a container for containing said liquid fragrance composition, said container having an orifice through which said composition may flow;
   (b) means for supporting said container in a position such that said orifice is beneath said liquid fragrance composition; and
   (c) a liquid permeable, microporous membrane secured within said orifice, said microporous membrane enabling said liquid fragrance composition to flow therethrough at a predetermined rate, said microporous membrane continually in contact with said liquid fragrance composition during the useful life of said dispenser, said liquid fragrance composition appearing, upon attainment of steady state equilibrium conditions, in liquid form on the exterior surface of said membrane and evaporating therefrom, the composition of said liquid form being at a given point in time substantially the same as that of the liquid fragrance composition remaining within the container, wherein the membrane is one through which the fragrance composition passes via liquid phase transmission and the character of the fragrance does not vary with time.

2. A dispenser according to claim 1 wherein said container further comprises a vent means to equalize the pressure between the interior and exterior of said container.

3. A dispenser according to claim 1 wherein said membrane further comprises an isotatic hydrophobic polypropylene having a thickness between approximately 1 and 5 mils and having no fillers, plasticizers or extenders.

4. A dispenser according to claim 1 further comprising an absorbent emanator pad in contiguity with said membrane to enable the liquid passing through said membrane to pass through said emanator pad by capillary action to increase the surface area from which said liquid may evaporate.

5. A dispenser according to claim 1 wherein said liquid fragrance composition contains at least one perfumery raw-material selected from the group consisting of: essential oils, products isolated from essential oils, products of animal origin and synthetic chemicals.

* * * * *